United States Patent
Palushaj

(10) Patent No.: US 10,849,660 B2
(45) Date of Patent: Dec. 1, 2020

(54) SANDING SCREEN DEVICE

(71) Applicant: Diamabrush LLC, Madison Heights, MI (US)

(72) Inventor: Simon Palushaj, Washington, MI (US)

(73) Assignee: Diamabrush LLC, Madison Heights, MI (US)

( * ) Notice: Subject to any disclaimer, the term of this patent is extended or adjusted under 35 U.S.C. 154(b) by 680 days.

(21) Appl. No.: 15/438,058

(22) Filed: Feb. 21, 2017

(65) Prior Publication Data
US 2018/0235661 A1 Aug. 23, 2018

(51) Int. Cl.
| | | |
|---|---|---|
| *B24D 3/00* | (2006.01) | |
| *B24D 15/02* | (2006.01) | |
| *B24D 18/00* | (2006.01) | |
| *B24D 3/28* | (2006.01) | |
| *B24D 15/04* | (2006.01) | |
| *A61B 17/54* | (2006.01) | |
| *A45D 29/00* | (2006.01) | |
| *A45D 29/04* | (2006.01) | |

(52) U.S. Cl.
CPC .............. *A61B 17/54* (2013.01); *A45D 29/00* (2013.01); *A45D 29/04* (2013.01); *B24D 3/007* (2013.01); *B24D 3/28* (2013.01); *B24D 15/02* (2013.01); *B24D 15/023* (2013.01); *B24D 15/04* (2013.01); *B24D 18/0009* (2013.01); *B24D 18/0081* (2013.01); *A45D 2029/045* (2013.01)

(58) Field of Classification Search
CPC .... B24D 3/007; B24D 15/02; B24D 18/0009; B24D 18/0081; A45D 29/00; A61B 2017/320008; A61B 17/320725
See application file for complete search history.

(56) References Cited

U.S. PATENT DOCUMENTS

| | | | |
|---|---|---|---|
| 2,740,239 A | 4/1956 | Ball et al. | |
| 2,876,086 A | 3/1959 | Raymond | |
| 2,984,052 A | 5/1961 | Mueller, Jr. | |
| 3,175,256 A * | 3/1965 | Horton | ...................... E06B 7/22 49/489.1 |
| 3,828,485 A | 8/1974 | McClure | |
| 3,860,400 A | 1/1975 | Prowse et al. | |
| 3,861,892 A | 1/1975 | Wisdom et al. | |
| 4,047,902 A | 9/1977 | Wiand | |

(Continued)

FOREIGN PATENT DOCUMENTS

EP 0439956 A2 8/1991

OTHER PUBLICATIONS

International Search Report and Written Opinion for PCT/US2018/018670 dated May 8, 2018 (14 pages).

*Primary Examiner* — Pegah Parvini
(74) *Attorney, Agent, or Firm* — Bejin Bieneman PLC

(57) ABSTRACT

A sanding device, for, e.g., cosmetic and finishing applications, is provided. The sanding device includes a wire mesh having a plurality of apexes, the apexes having an abrasive affixed thereto. The wire mesh forms a substantially planar surface with a bent perimeter section. The sanding device further includes a rim made from a plastic material, the plastic material capping the bent perimeter section of the wire mesh and further extending from the bent perimeter section. The wire mesh and the rim defining a shallow bowl shape. The sanding devices also includes a carrier shell or grip received and captured with the bowl shape.

11 Claims, 10 Drawing Sheets

(56) References Cited

U.S. PATENT DOCUMENTS

| | | | |
|---|---|---|---|
| 4,282,011 A | 8/1981 | Terpay | |
| 4,314,589 A | 2/1982 | Buchanan et al. | |
| 4,949,511 A | 8/1990 | Endo et al. | |
| 4,974,642 A | 12/1990 | Taipale | |
| 5,131,924 A | 7/1992 | Wiand | |
| 5,203,881 A | 4/1993 | Wiand | |
| 5,997,221 A * | 12/1999 | Sadler | B23D 71/06 407/29.1 |
| 6,024,634 A | 2/2000 | Hoglund et al. | |
| 6,383,064 B1 | 5/2002 | Eggert et al. | |
| 6,419,572 B2 | 7/2002 | Moore | |
| 6,482,308 B1 | 11/2002 | Wiemann | |
| 6,672,952 B1 | 1/2004 | Masmar et al. | |
| 7,108,019 B2 | 9/2006 | Nagura et al. | |
| 7,258,705 B2 | 8/2007 | Woo et al. | |
| 7,336,500 B1 * | 2/2008 | Negron | G09B 23/186 174/521 |
| 7,438,635 B2 | 10/2008 | Hoglund | |
| 7,517,277 B2 | 4/2009 | Muldowney | |
| 2002/0153019 A1 | 10/2002 | Ayzman | |
| 2003/0013397 A1 | 1/2003 | Rhoades | |
| 2008/0220703 A1 | 9/2008 | Jung | |
| 2009/0245709 A1 * | 10/2009 | Murakami | C08G 59/38 384/548 |
| 2011/0104999 A1 | 5/2011 | Palushaj et al. | |
| 2013/0295821 A1 * | 11/2013 | Lugg | B24B 37/245 451/59 |
| 2014/0338687 A1 * | 11/2014 | Haynes | A61B 17/54 132/76.4 |
| 2015/0297261 A1 | 10/2015 | Comstock et al. | |

* cited by examiner

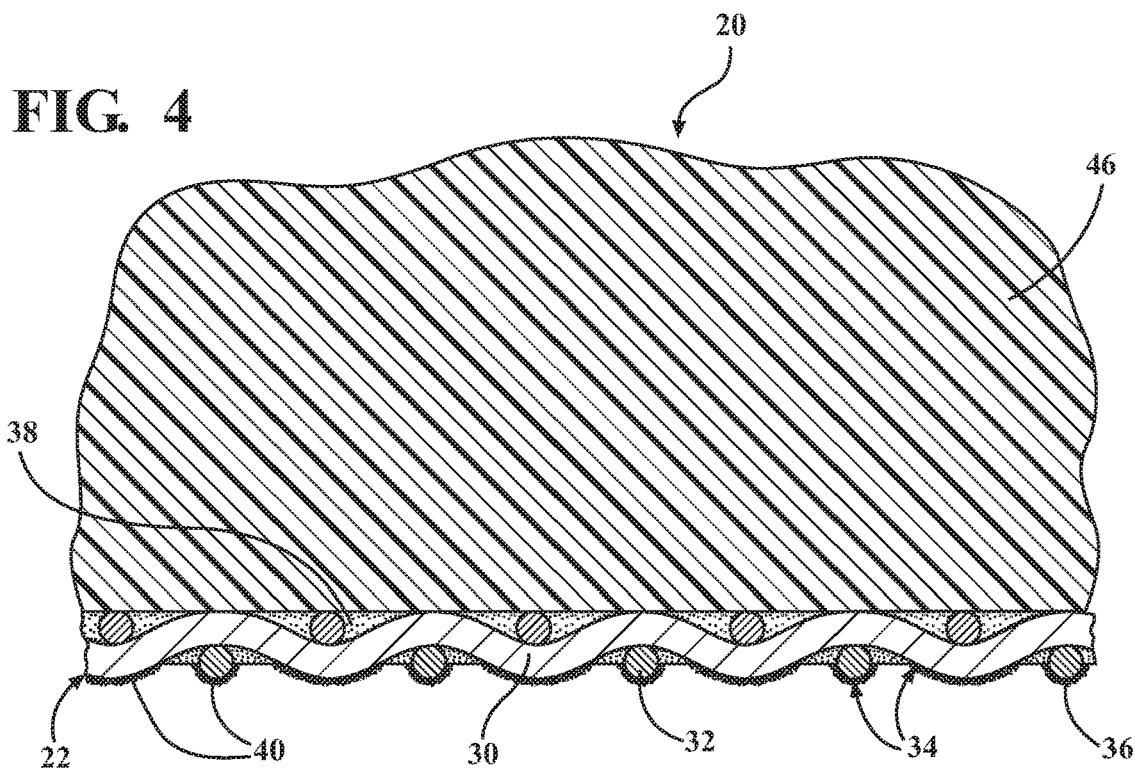
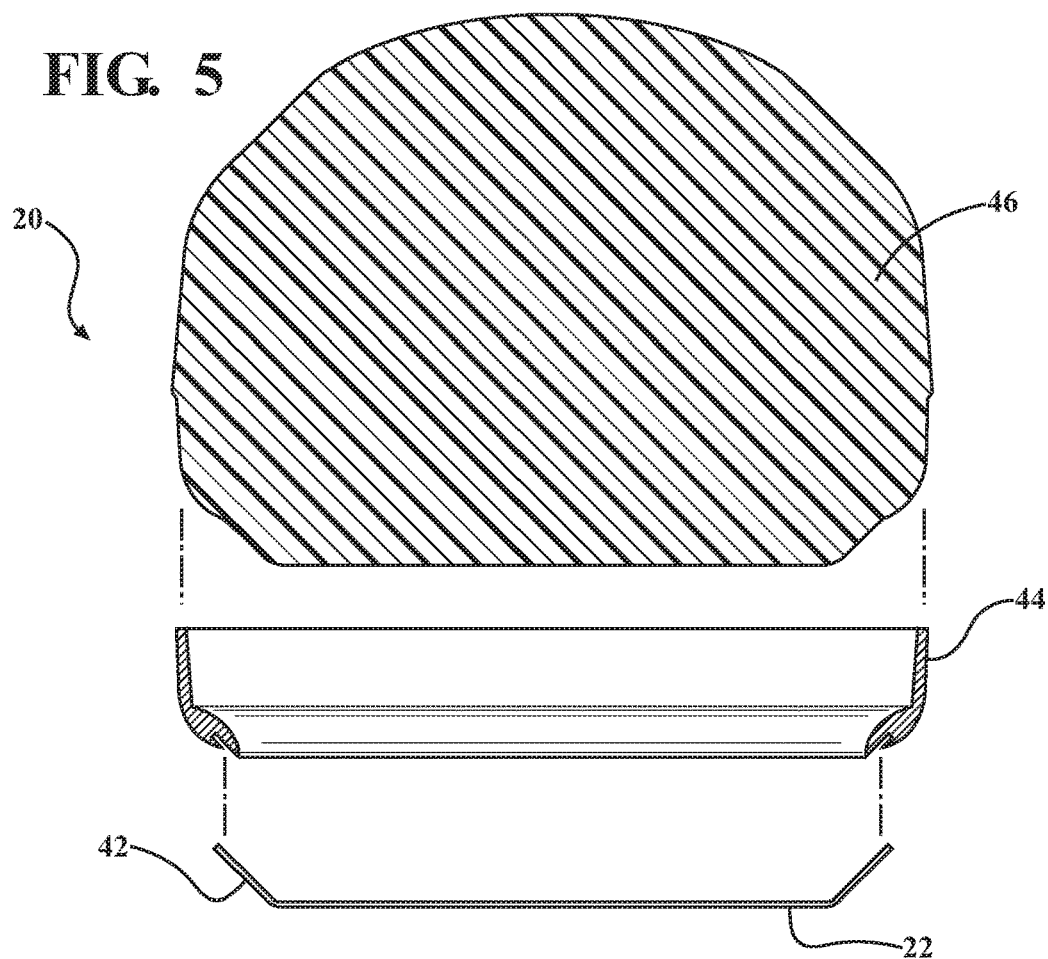

SANDING SCREEN DEVICE

BACKGROUND

Hand held abrasive tools have many applications, resulting in demand for various improvements related, e.g., to the different users, applications, markets, and distribution channels, respectively. For example, the range of settings for using abrasive tools extends, by way of example, from commercial and industrial applications, e.g., concrete polishing and component finishing, to consumer applications, e.g. personal skin care.

In response to such demands, Applicant has developed improvements for abrasive tools. However, given the variety of needs from, e.g., different users, applications, markets, and distribution channels, respectively, demand for improved abrasive tools such as sanding screens continues. For example, devices including sanding screens may fray along the perimeter over a period of time, and, it is currently difficult to inhibit or mitigate such wear.

BRIEF DESCRIPTION OF THE DRAWINGS

FIG. 4 is an enlarged view of a portion of the cross-sectional view of the exemplary sanding device of FIG. 3;

FIG. 5 is an exploded cross-sectional view of the exemplary sanding device of FIGS. 1-3;

DETAILED DESCRIPTION

Among the features described herein, a sanding screen device according to the principles of the present disclosure includes a protective rim that encapsulates the perimeter of the screen component to inhibit fraying of the wires at the perimeter. A sanding screen device according to the principles of the present disclosure may also include an exposed, i.e. chamfered or cutaway, corner of the bottom of the body component supporting the screen component, that allows the screen component to extend away from its abrasive base surface. Such an exposed or cutaway corner also may provide a sanding screen device according to the principles of the present disclosure to be used more efficiently at an angle, e.g. during use as a foot scrubber, sanding wheel or grill brush.

Figure 1:
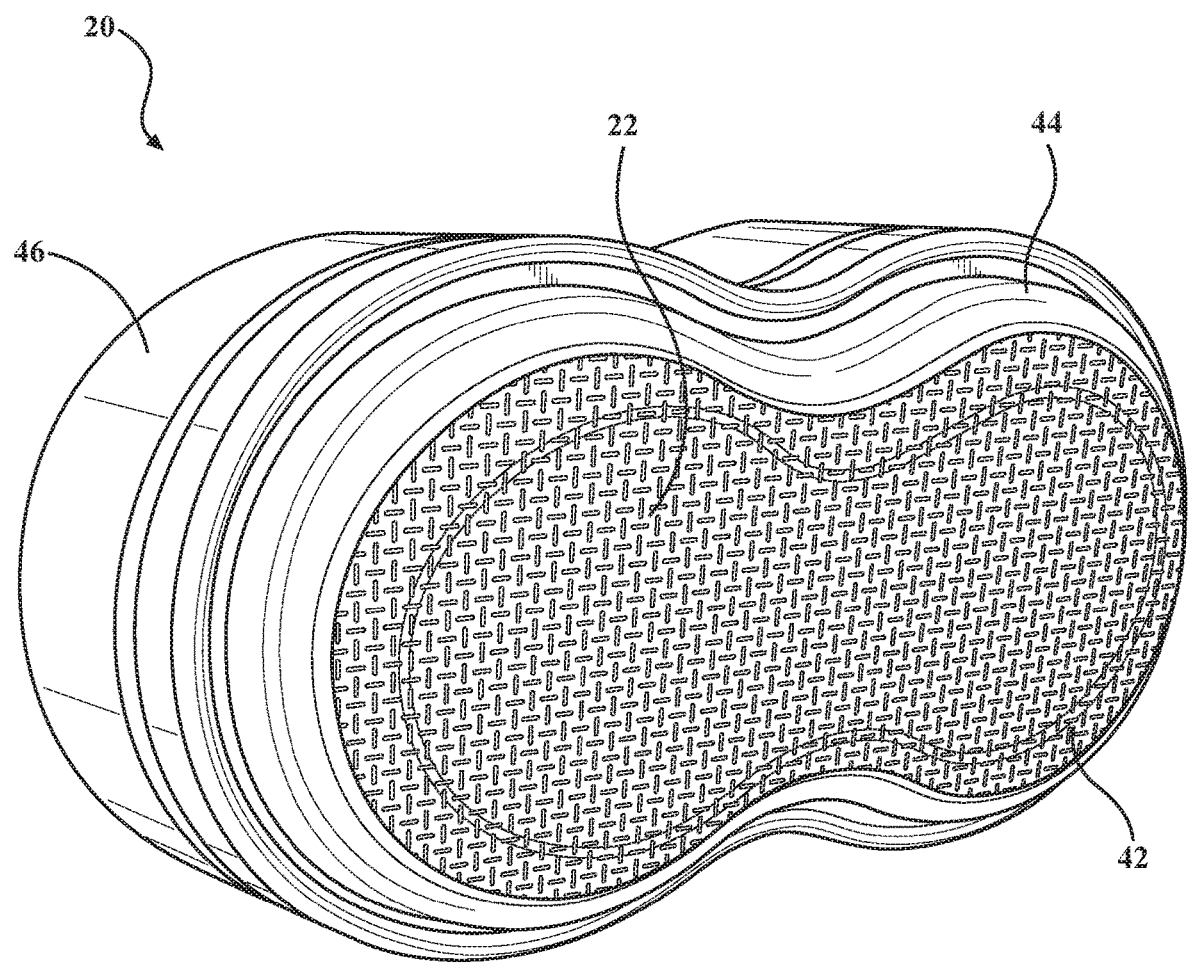
FIG. 1 is a bottom perspective view of an exemplary sanding device in the form of a foot scrubber for use in, e.g., pedicures.
Figure 2:
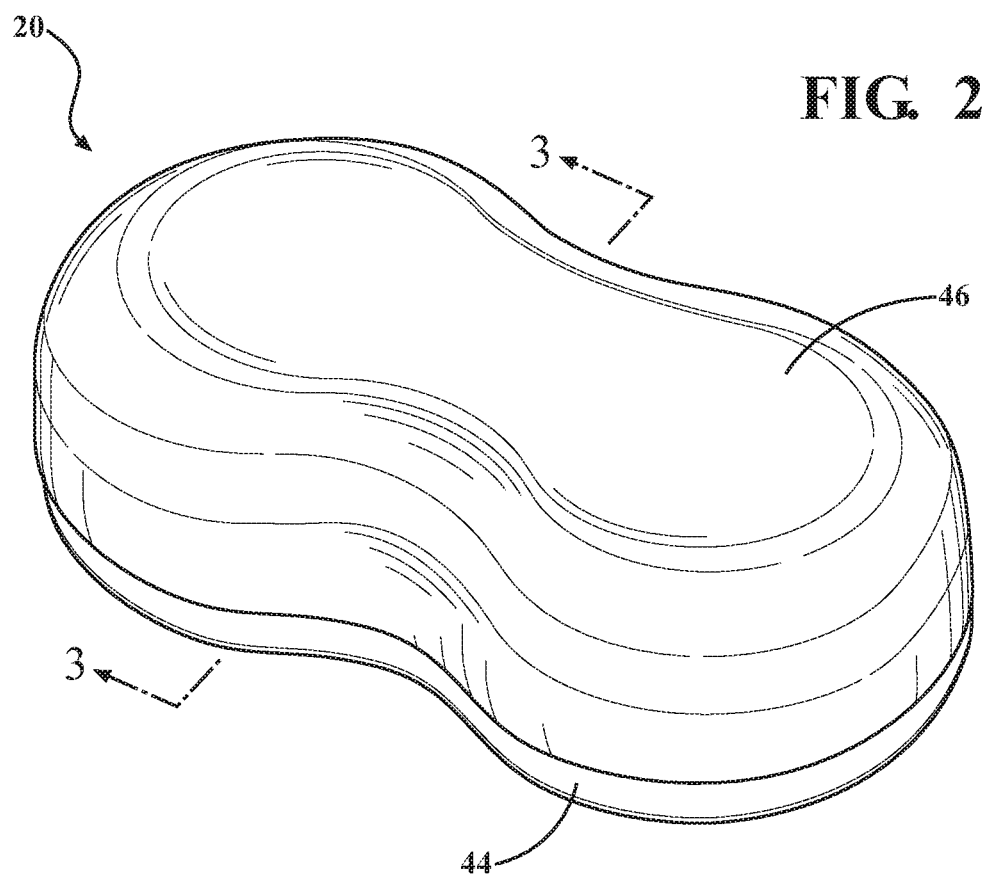
FIG. 2 is a top perspective view of the exemplary sanding device of FIG. 1.

With reference to the figures, wherein like elements are numbered alike, there is shown exemplary sanding screen devices a mold assembly used to manufacture a sanding screen according to the principles of the present disclosure. With reference to FIGS. 1-2, a sanding device 20, in the form of a foot scrubber, includes a foam grip 46. Foot scrubber 20 includes a sanding screen 22 fastened to foam grip 46 via a rim 44. As shown screen 22 includes a bent section 42 in a lip configuration that offsets screen 22 away from grip 46. The offset allows for foot scrubber 20 to be used at a variety of different angles.

Figure 3:
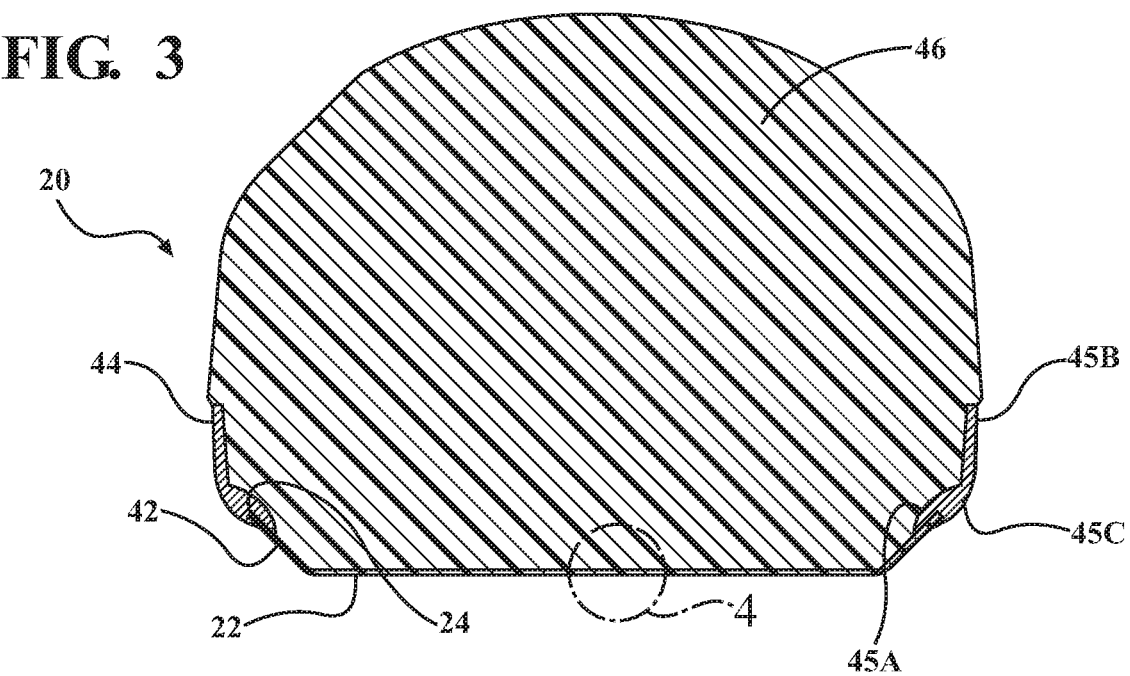
FIG. 3 is a cross-sectional view of the exemplary sanding device of FIGS. 1-2 alone the line 3-3 of FIG. 2.

FIG. 3 is a cross sectional drawing along the line 3-3 of FIG. 2. The rim 44 includes a first leg 45A and a second leg 45B separated by a corner section 45C, with the first and second legs 45A, 45B encapsulating a perimeter 24 of the sanding screen 22. With additional reference to FIGS. 4 and 5, encapsulation of the perimeter 24 of sanding screen 22 protects the perimeter 24 and inhibits fraying of the sanding screen 22 at the perimeter 24. Rim 44 may be made of vinyl and can be molded to screen 22 as described in greater detail below. First leg 45A encapsulates perimeter 24 and second leg 45B captures grip 46 as described in greater detail below.

Grip 46 is relatively rigid in comparison to the screen 22, i.e., in the foot scrubber 20, grip 46 is configured to maintain or be resilient to manual forces applied to a foot. For example, in some embodiments, grip 46 is made from a non-porous material, such as closed cell foam, and, in another example, urethane.

FIG. 4 is a close up at section 4 of FIG. 3—an enlarged portion of the cross section of screen 22. Screen 22 includes interlaced wire mesh 28, including row wires 30 and column wires 32. According to the principles of the present disclosure, the wire mesh size may vary according to user preferences and/or application requirements, e.g. fine mesh for cosmetic applications such as skin care. Wire mesh 28 include outer arcuate sections 34, in both the rows and the columns, respectively, each section having an outer apex 36. For example, with the wire mesh 28 in a lip configuration with the bent section 42, the outer surface of the wire mesh 28 is the convex exterior surface providing the abrasive interface The second, inner or concave surface is configured to directly interface with the grip 46, as disclosed herein. The sanding device 20 includes a resin 38 partially coating wire mesh 28. The outer apex 36 of each respective outer arcuate section 34 is outside of the resin 38, i.e. free of coating. Resin 38 is a nonconductive coating and, in some embodiments, may be a resilient, flexible material. For example, where the screen 22 is used in connection with foot scrubber 20, the resin is a food-grade polyester resin, such as the resin designated as Ashland 7241-T-15.

The exposed outer apexes 36 are affixed with an abrasive 40 to provide desired sanding characteristics. Wire mesh 28 includes a metallic material, such as aluminum, steel, or stainless steel. It should be understood that other known screen materials and alloys may also be utilized in accordance with the principles of the present invention. In some embodiments, the abrasive 40 is diamond and is plated on the apexes 36. In other embodiments, the abrasive 40 may be Cubic Boron Nitride. The sanding device 20 is provided with a grit size according to the intended application thereof, e.g. a fine grit for cosmetic applications such as skin care.

Figure 11:
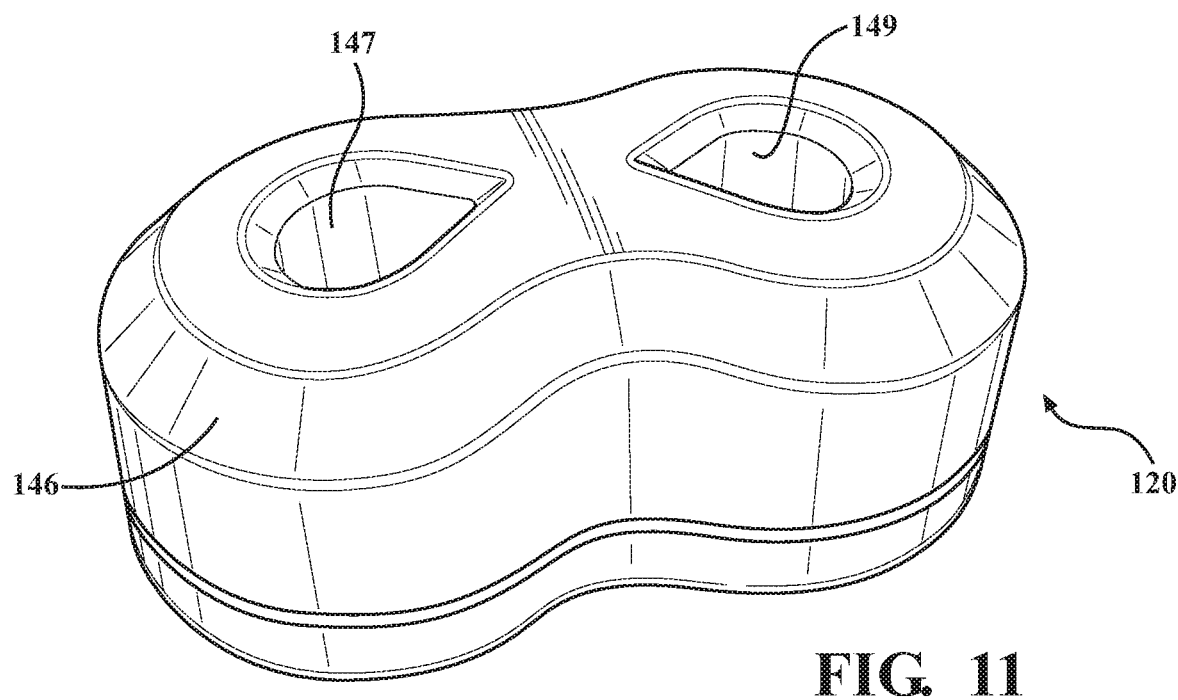
FIG. 11 is a perspective view of another exemplary sanding device.
Figure 12:
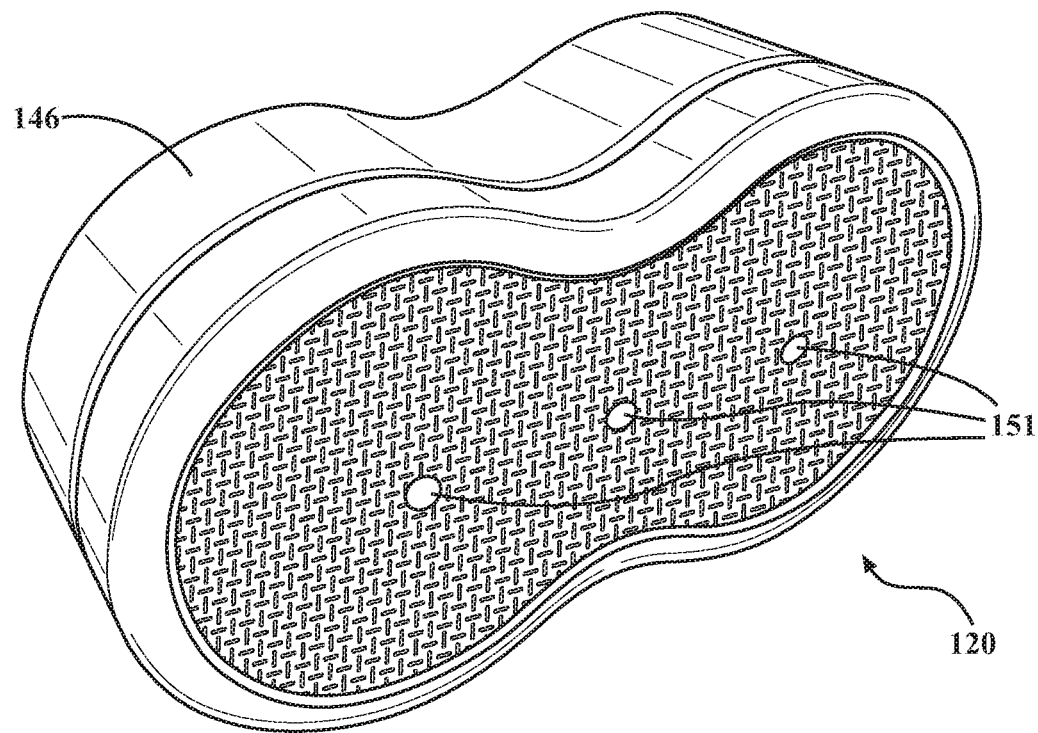
FIG. 12 is a bottom perspective view of the exemplary sanding device of FIG. 11.
Figure 13:
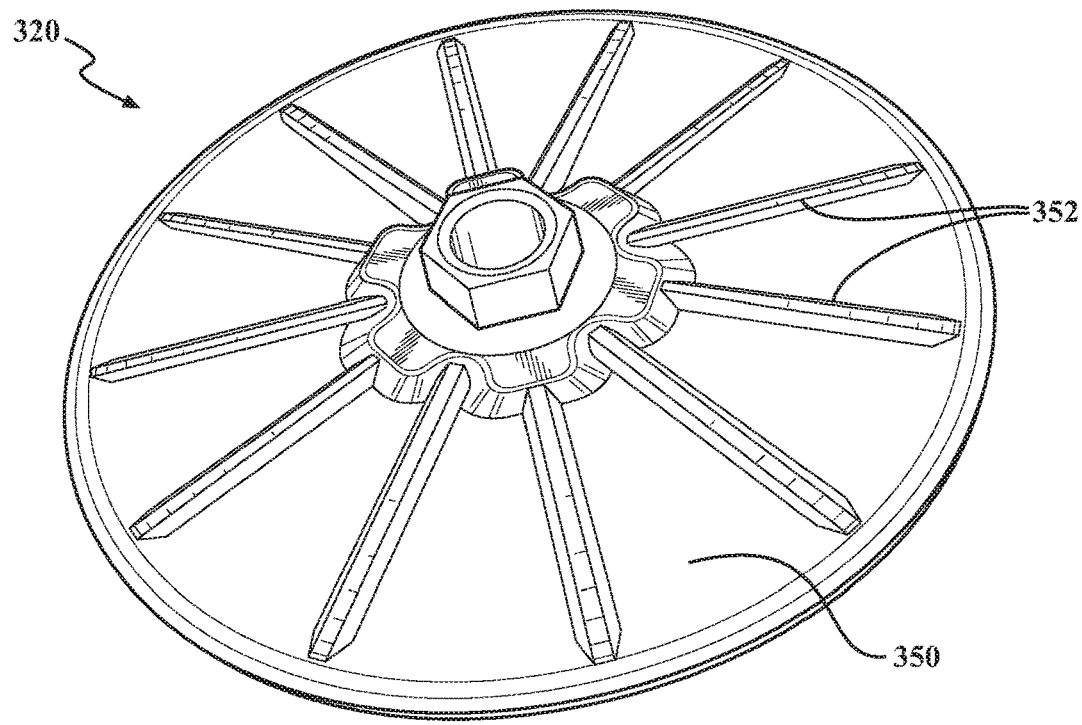
FIG. 13 is a perspective view of an exemplary sanding wheel according to the principles of the present disclosure.
Figure 14:
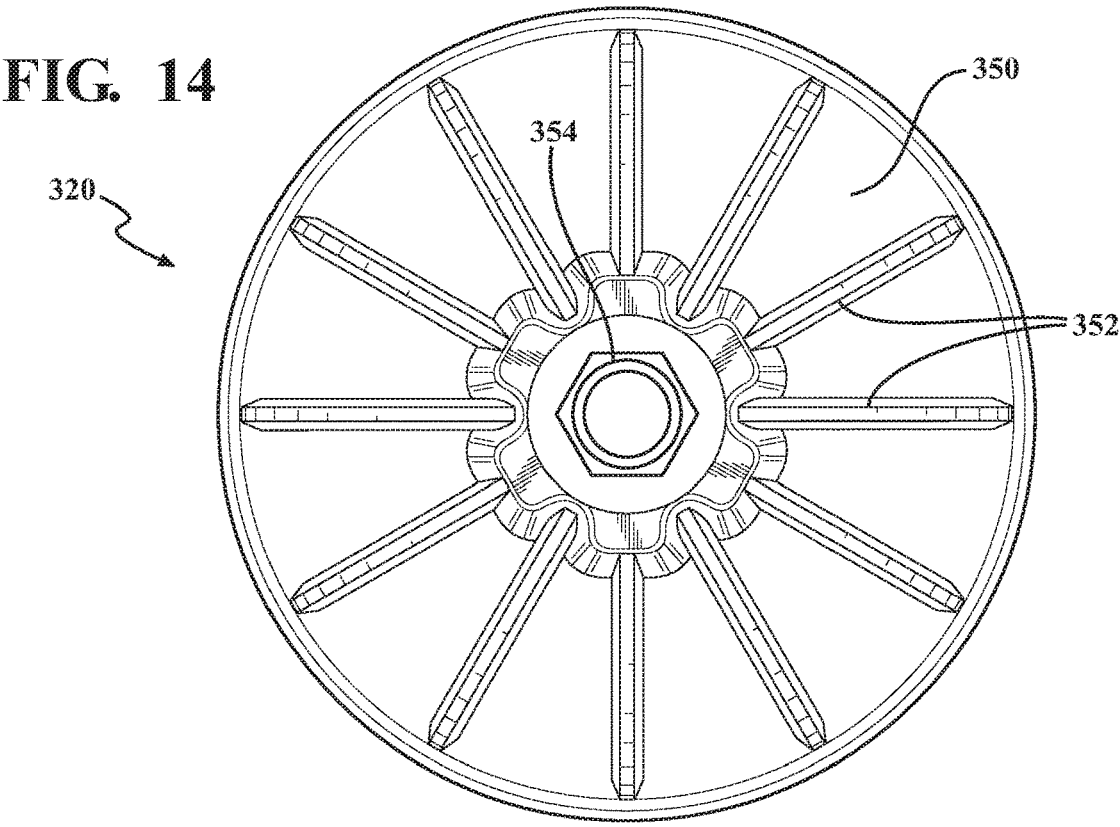
FIG. 14 is a top view of the sanding wheel of FIG. 12.
Figure 15:
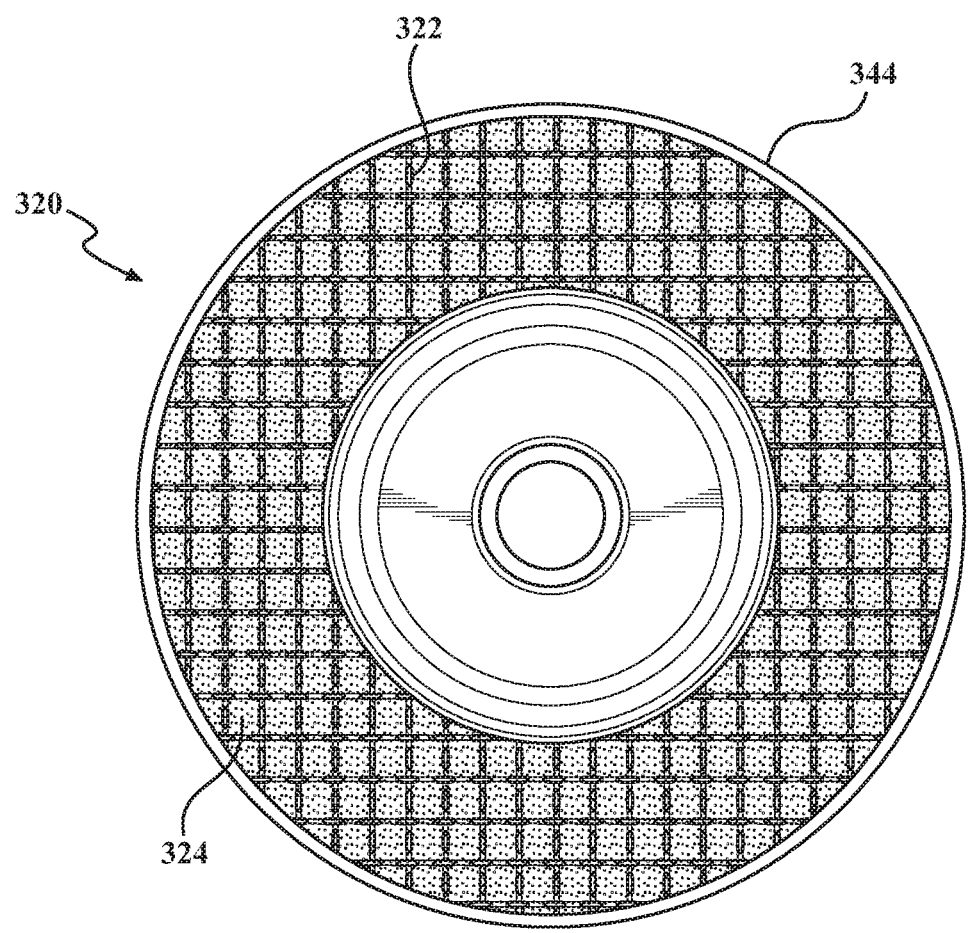
FIG. 15 is a bottom view of the sanding wheel of FIG. 12.
Figure 16:
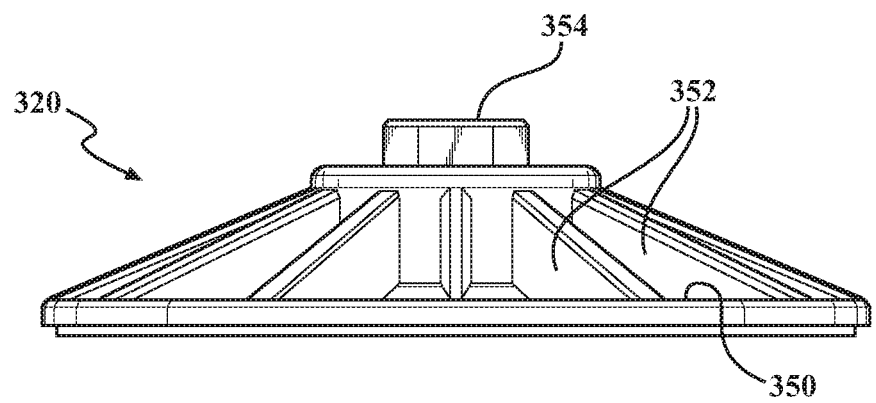
FIG. 16 is a side view of the sanding wheel of FIG. 12.

FIGS. 11-12 show another sanding device 120 in the form of a foot scrubber according to the principles of the present disclosure. It should be understood that, unless otherwise set forth herein, the description of the sanding device 20 and its components is applicable to foot scrubber 120. Foot scrubber 120 includes a grip 146 including a pair of apertures 147 and 149, and fluidly coupled outlets 151 providing paths for water to pass through during use of the foot scrubber 120. For example, in some exemplary applications of a sanding device according to the principles of the present disclosure, water is used to clear debris during sanding and/or lower the temperature of the surface being sanded. In another example for sanding of, e.g., metallic surfaces, use of water allows for a finish with a relatively greater amount of polish—e.g., wet sanding applications for aerospace and automotive component finishing.

Figure 6:
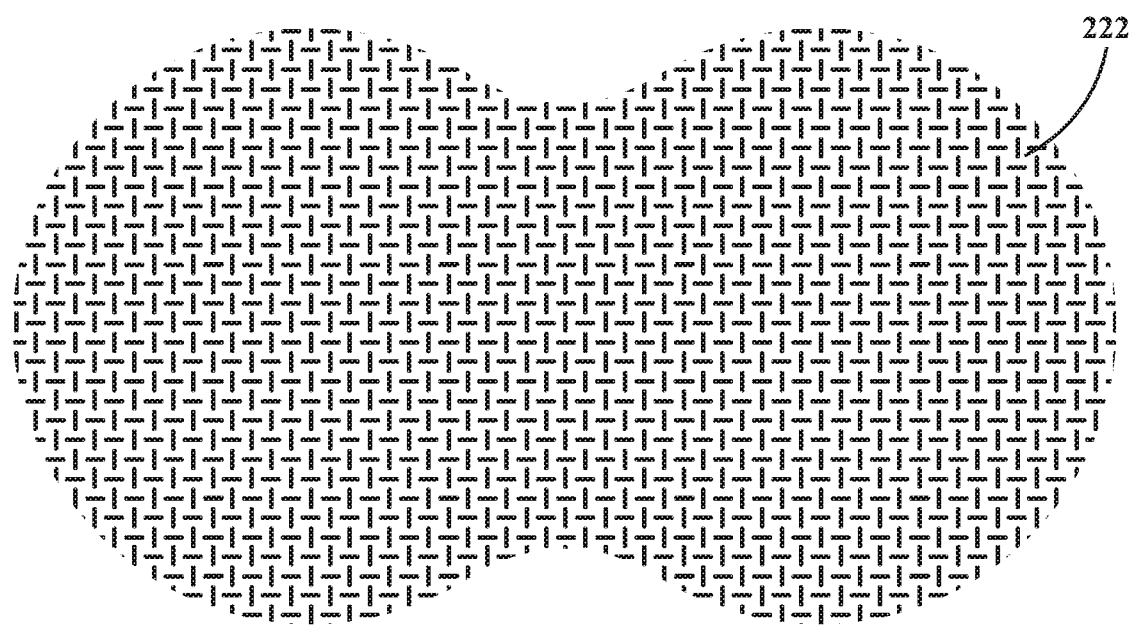
FIG. 6 is a plan view of a screen component for the exemplary sanding device of FIGS. 1-3.
Figure 10:
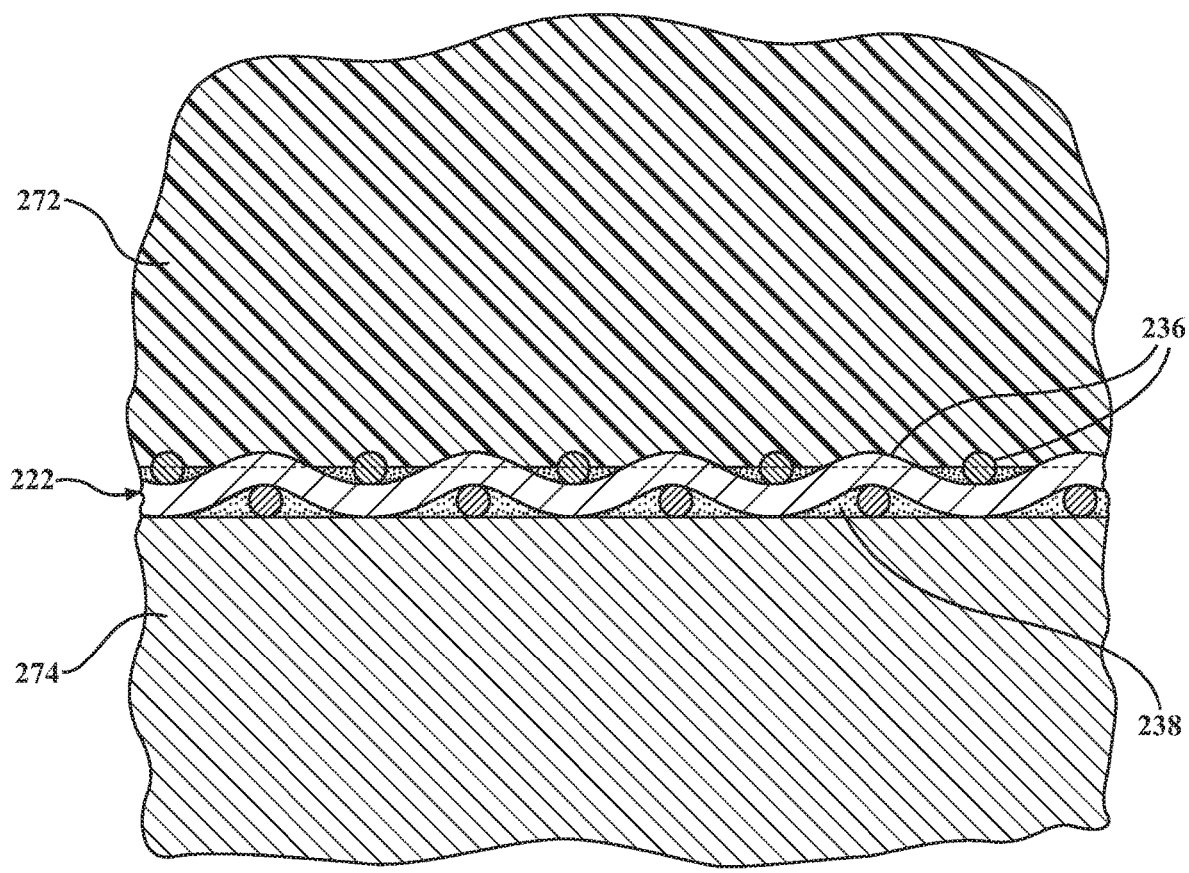
FIG. 10 is a partial cross sectional view of the first and second mold components of FIG. 10 coupled together about the screen component with a coating material further disposed therebetween.

With reference to FIGS. 6 and 10, an uncoated screen component 222 and a mold which may be used to apply resin to the uncoated screen 222 are shown, in whole or part. The mold includes an upper mold 272 and a lower mold 274. The upper mold 272 is a relative soft or flexible mask component made from, e.g., silicon, and lower mold 74 is relatively rigid (compared to mask component) and is made from, e.g., steel. With particular reference to FIG. 10, uncoated screen 222 is placed in between the lower mold 274 and upper mold 272. The upper mold 272 is directly pressed against uncoated screen 222. Upper mold 272 resiliently deforms against screen, to mask apexes 236 of the screen 222 such that when a resin 238 is injected into the mold, between the upper and lower molds 272, 274, it does not cover those apexes 236 protected by upper mold 272. The upper mold 272 may be varied in material composition so as to provide higher durometer characteristics to leave correspondingly less of screen 222 exposed and lower durometer characteristics to leave more of screen 222 exposed. Where more of screen 222 is exposed more abrasive, such as abrasive 40 disclosed herein, may be bonded thereto, e.g. such as described herein with respect to sanding device 20 and screen 22.

According to the principles of the present disclosure, it should be understood that alternate methods may be used to prepare a partially coat screen 222. For example, in another embodiment screen 222 may initially be entirely coated with resin. The resin may then be removed via a sanding, or other, operation to expose bare metal at the apex sections which may then, in turn, have an abrasive plated thereto.

In some embodiments, the resin coating the screen is made of silicone material. It should be understood that, according to the principles of the present disclosure, resin composition may be varied to provide particular desirable performance characteristics. For example, a high temperature resin, e.g. a silicone material may act as a heat barrier that will improve sanding efficiency by resisting heating generated by a sanding operation. Further, resins, or variations in the material compositions thereof, may impart improved flexibility of the coating screen thereby allowing sanding screen to conform to the shape of the material being sanded.

In one embodiment, screen 222 may be a sheet to which a resin will be applied and then cut into various shapes for use with different sanding tools. For example, referring to FIG. 6, one shape may conform to the shape of the foot scrubber 20 shown in FIG. 1. Alternate shapes may be available. When a shape is cut the metal ends of the screen are exposed and may fray. In one embodiment, a corner 42 is bent adjacent the perimeter 24 of the screen.

Figure 7:
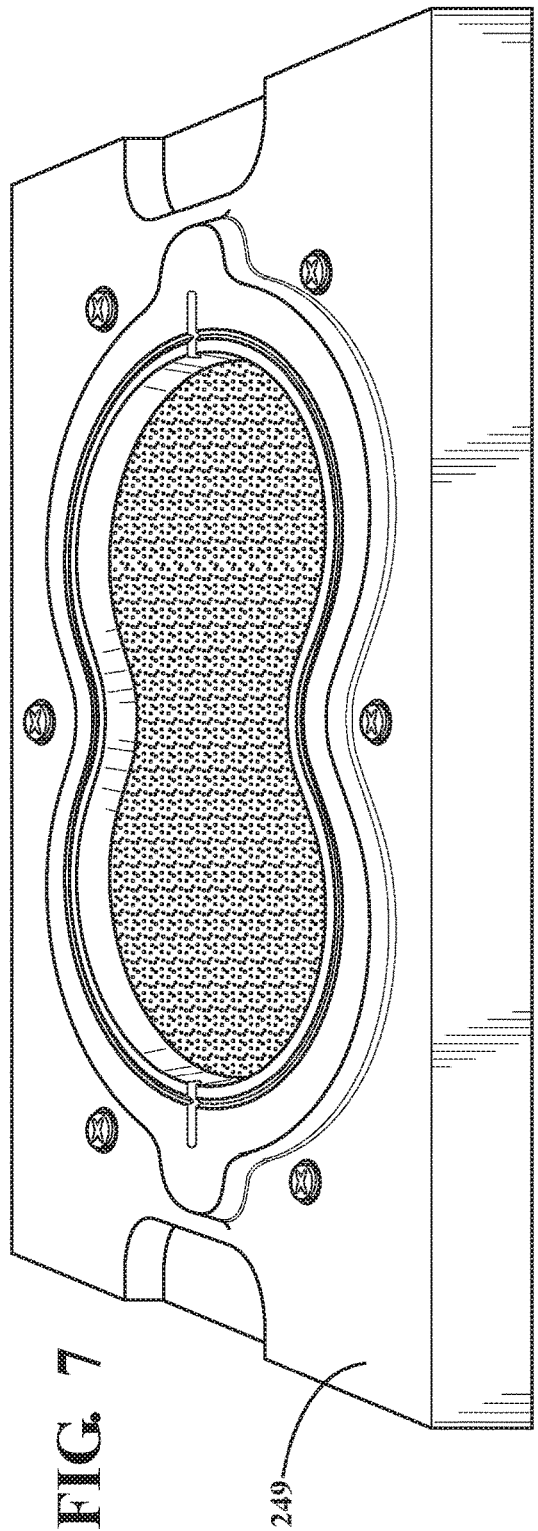
FIG. 7 is a perspective view of a first mold component for partial coating of a screen component according to the principles of the present disclosure.
Figure 8:
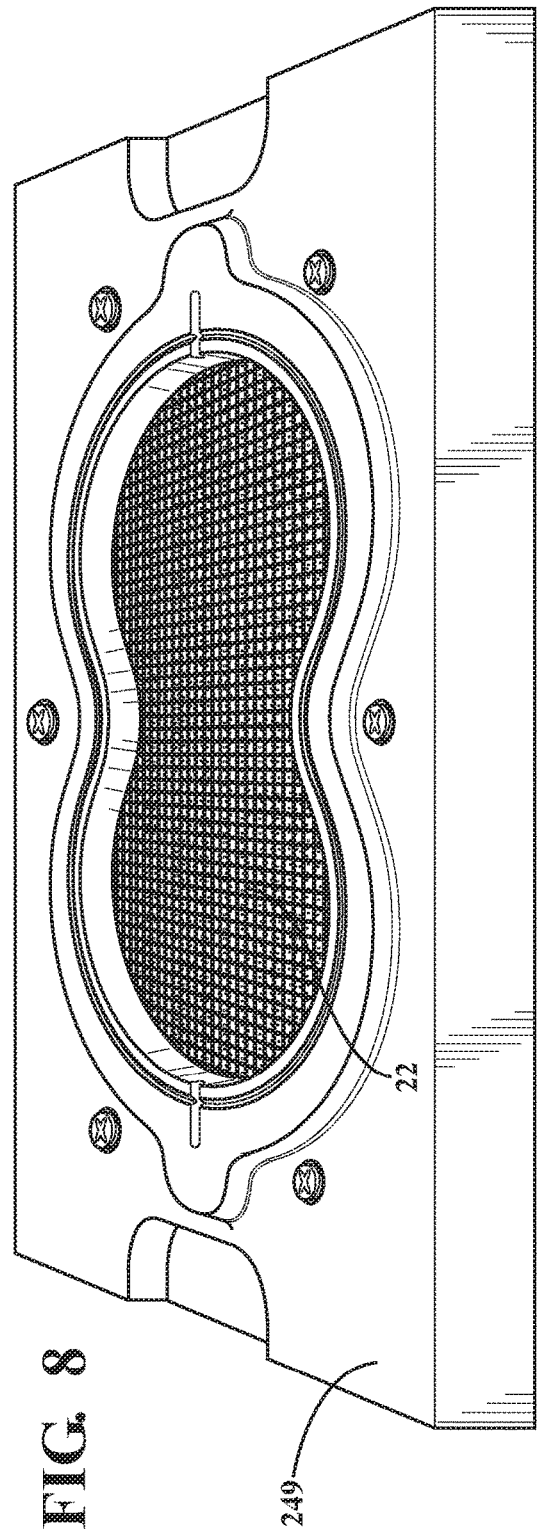
FIG. 8 is a perspective view of the first mold component of FIG. 7 with a screen component disposed therein.
Figure 9:
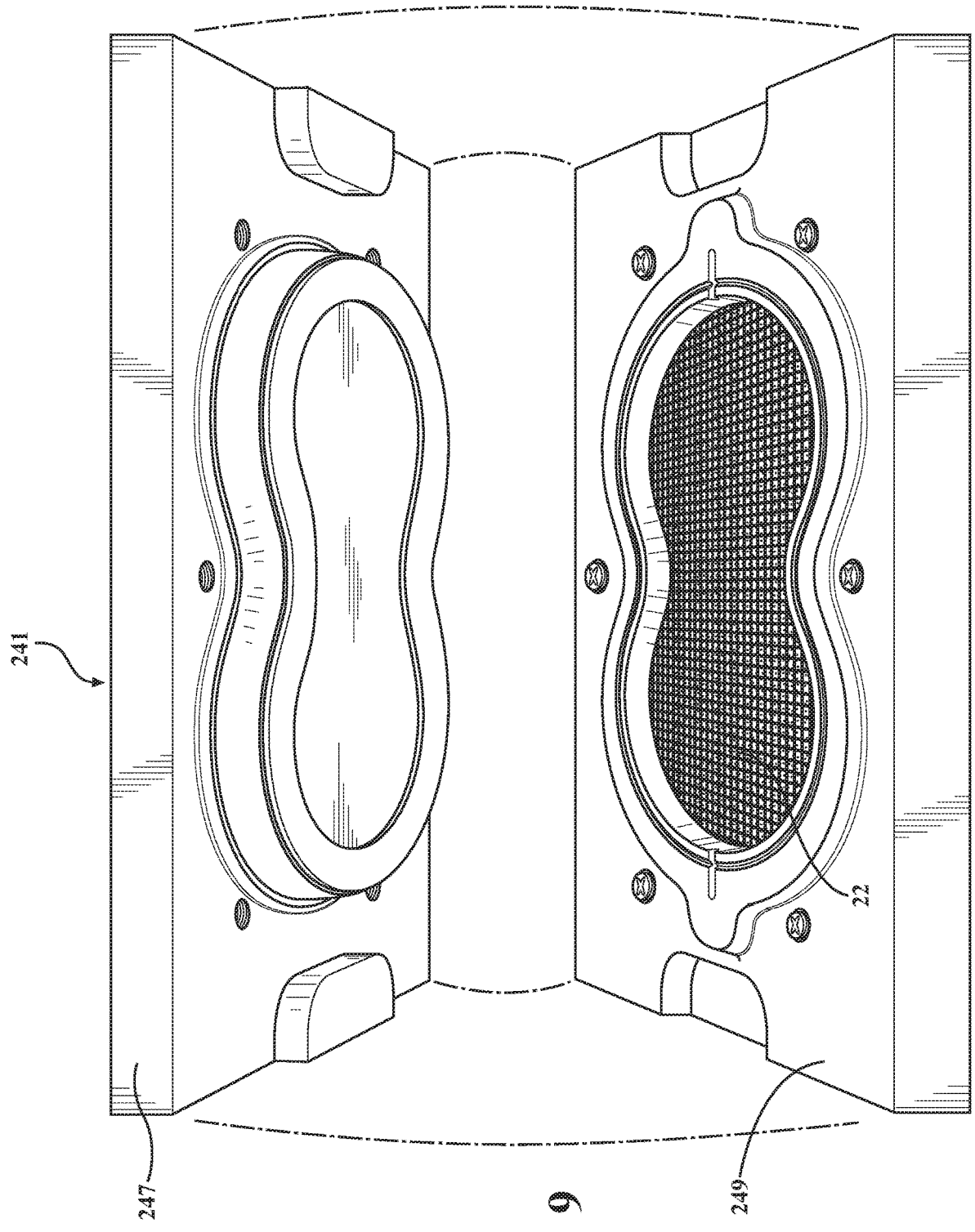
FIG. 9 is a perspective view of the first mold component and screen component of FIG. 8, with a second mold component for partial coating of the screen component according to the principles of the present disclosure.

With reference to FIG. 7-9, there is shown a rim mold 241 which may be used to form the rim 44. The rim mold 241 includes a male mold 247 and a female mold 249. The mold 241 is metallic, e.g. aluminum or steel. With particular reference to FIGS. 8-9, female mold 249 is shown. Female mold 249 includes a platen 251 made from, e.g., a relatively soft material, such as silicone. The screen 22 may be placed into female mold 249 with the exposed apexes interfacing with the platen 251. With further reference to FIG. 10, the female mold 249 receives the male mold 247. received thereby.

With male mold 247 and female mold 249 sandwiching screen 22, a resin is injected into the mold and fills a chamber therein extending around and about the perimeter 24 of screen 22. The mold is configured so that the chamber corresponds to the shape of rim 44, where rim 44 encapsulates the perimeter 24 of screen 22, as, e.g, shown in FIGS. 3, 5 rim 44 includes first leg 46 and second leg 48. Finally, the grip 46 is formed on the screen 22 and rim 44. For example, in some embodiments, the screen 22 and rim 44 are be placed in a mold (not shown) such that material for the grip 46 (e.g. foam) maybe injected to form the grip 46.

With reference to FIGS. 13-16, a device in the form of a sanding wheel 320 includes a screen 322 (FIG. 15) according to the principles of the present disclosure. It should be understood that, with exception to the configuration of the screens relative to the body components of the respective sanding devices, the description herein of the screen 22 is applicable to the screen 322. In some implementations, the screen 322 may include a resin material that is relatively more heat resistant than the resins described with respect to the screen 22. By way of example, in some implementations, the screen 322 includes a heat resistant polyester resin such as Hetron FR998-25 VE resin.

In some implementations, the sanding wheel 320 includes a backing component 324 for the screen 22. The backing component 324 is, e.g., made of a fiberglass material, such as a Vectoply ELT 18700-7P (18 oz.) material. The backing component 324 and the screen 322 are secured together, such as with a high temperature adhesive. In some implementations, the assembly of the backing component 324 and the screen 322 has a convexly outward bent portion at the perimeter, such as that described with respect to screen 22. Furthermore, in some implementations, the sanding wheel 320 further includes a rim 344 around the edge of the screen 322 and the backing component 324. The rim 344 may be formed, e.g., in a mold as described with respect to the rim 44 and screen 22 herein. In other implementations, the rim 344 may be formed on the screen 322 prior to attachment of the backing component 324.

The sanding wheel 320 also includes a hub 350. In an exemplary implementation, the hub 350 includes a plurality of spoke members 352 which provide rigidity to the hub 350 and, thereby, the sanding wheel 320. A coupling member 354, e.g. a fixed threaded fastener, is included to facilitate attachment of the sanding wheel 320 to a tool, such as a high speed grinder (not shown) or a drill (not shown).

It should be understood that the above description is intended to be illustrative and not restrictive. Many embodiments and applications in accordance with the principles of the present disclosure, in addition to the examples provided, would be apparent upon reading the above description. It is anticipated and intended that future developments will occur in the technologies discussed herein, and that the disclosed devices, systems and methods will be incorporated into such future embodiments. In sum, it should be understood that the teachings of the present disclosure are capable of modification and variation.

All terms used in the claims are intended to be given their ordinary meanings as understood by those knowledgeable in the technologies described herein unless an explicit indication to the contrary is made herein. In particular, use of the singular articles such as "a," "the," "said," etc. should be read to recite one or more of the indicated elements unless a claim recites an explicit limitation to the contrary.

The Abstract is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

The invention claimed is:

1. An apparatus comprising:
   a grip component;
   a sanding screen layer fixed to the grip component and having an exterior surface and a perimeter edge defining a complementary shape to the grip component; and
   a rim extending about the grip and encapsulating the perimeter edge of the sanding screen layer,
   wherein the sanding screen layer includes a sheet of a resin material and a wire mesh, the exterior surface of the sanding screen layer including a plurality of exposed outer apexes of the wire mesh free of the resin material, the sanding screen layer further including an abrasive material bonded to the exposed outer apexes of the wire mesh across the exterior surface, wherein there is at least one through aperture extending through the grip component and the sanding screen layer, the through aperture configured to provide a path for water to pass.

2. The apparatus of claim 1, wherein the sanding screen layer has a lip including the perimeter edge, the exterior surface extending over a convex exterior of the sanding screen layer at the lip.

3. The apparatus of claim 2, wherein the sanding screen layer and the rim define a bowl shape.

4. The apparatus of claim 3, wherein the rim includes vinyl material.

5. The apparatus of claim 1, wherein the resin material includes silicone material.

6. The apparatus of claim 1, wherein the grip component is made of a non-porous material.

7. A cosmetic sanding device comprising:
   a sanding screen including a sheet of a resin material and a wire mesh, the wire mesh having a plurality of apexes extending outside of the resin material across an exterior surface of the sanding screen, the apexes having an abrasive affixed thereto; the exterior surface of sanding screen having a substantially planar section and a bent perimeter section;
   a rim made from a plastic material, the plastic material capping the bent perimeter section of the sanding screen and further extending from the bent perimeter section, the sanding screen and the rim defining a shallow bowl shape; and
   a carrier shell being received and captured with the bowl shape, wherein there is at least one through aperture extending through the carrier shell, the through aperture configured to provide a path for water pass.

8. The cosmetic sanding device of claim 7, wherein the resin material includes silicone material.

9. The cosmetic sanding device of claim 7, wherein the resin coating is a polyester.

10. The cosmetic sanding device of claim 8, wherein the carrier shell is made from urethane.

11. The cosmetic sanding device of claim 10, wherein the carrier shell comprises an upper surface and a bottom surface where the bottom surface of the shell is adjacent to the wire mesh.

* * * * *